United States Patent
Alwan et al.

(10) Patent No.: US 9,968,283 B2
(45) Date of Patent: *May 15, 2018

(54) SYSTEM AND METHOD FOR THE INFERENCE OF ACTIVITIES OF DAILY LIVING AND INSTRUMENTAL ACTIVITIES OF DAILY LIVING AUTOMATICALLY

(71) Applicant: University of Virginia Patent Foundation, Charlottesville, VA (US)

(72) Inventors: Majd Alwan, Charlottesville, VA (US); Robin A. Felder, Charlottesville, VA (US); Steven W. Kell, Keswick, VA (US); Sarah G. Wood, Lovingston, VA (US); Michael Cvetanovich, Charlottesville, VA (US); Beverly L. Turner, North Garden, VA (US); J. William Holman, Earlysville, VA (US)

(73) Assignee: University of Virgina Patent Foundation, Charlottesville, VA (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 14/551,882

(22) Filed: Nov. 24, 2014

(65) Prior Publication Data

US 2015/0080767 A1    Mar. 19, 2015

Related U.S. Application Data

(63) Continuation of application No. 11/076,604, filed on Mar. 10, 2005, now Pat. No. 8,894,576.

(Continued)

(51) Int. Cl.
*A61B 5/00* (2006.01)
*A61B 5/11* (2006.01)
*A61B 5/20* (2006.01)

(52) U.S. Cl.
CPC .......... *A61B 5/1115* (2013.01); *A61B 5/0002* (2013.01); *A61B 5/1112* (2013.01);
(Continued)

(58) Field of Classification Search
CPC ... A61B 5/1115; A61B 5/0002; A61B 5/1112; A61B 5/1113; A61B 5/1116;
(Continued)

(56) References Cited

U.S. PATENT DOCUMENTS

5,410,471 A * 4/1995 Alyfuku et al. .............. 600/300
5,692,215 A * 11/1997 Kutzik et al. .................. 710/18
(Continued)

*Primary Examiner* — David C Eastwood
*Assistant Examiner* — Shirley Jian
(74) *Attorney, Agent, or Firm* — Robert J. Decker; Tanner IP, PLLC (57) ABSTRACT

A method and related system to, among other things, automatically infer answers to all of the ADL questions and the first four questions of the IADL in the home. The inference methods detect the relevant activities unobtrusively, continuously, accurately, objectively, quantifiably and without relying on the patient's own memory (which may be fading due to aging or an existing health condition, such as Traumatic Brain Injury (TBI)) or on a caregiver's subjective report. The methods rely on the judicious placement of a number of sensors in the subject's place of residence, including motion detection sensors in every room, the decomposition of each relevant activity into the sub-tasks involved, identification of additional sensors required to detect the relevant sub-tasks and spatial-temporal conditions between the signals of sensors to formulate the rules that will detect the occurrence of the specific activities of interest.

20 Claims, 2 Drawing Sheets

Related U.S. Application Data (60) Provisional application No. 60/551,894, filed on Mar. 10, 2004.

(52) U.S. Cl.
CPC ........... *A61B 5/1113* (2013.01); *A61B 5/1116* (2013.01); *A61B 5/202* (2013.01); *A61B 5/6887* (2013.01); *A61B 5/6889* (2013.01); *A61B 5/7282* (2013.01); *A61B 2560/0242* (2013.01); *A61B 2562/0247* (2013.01); *A61B 2562/046* (2013.01)

(58) Field of Classification Search
CPC ....... A61B 5/202; A61B 5/6887; A61B 5/688; A61B 5/09; A61B 5/7282; A61B 2560/0242; A61B 2562/0247; A61B 2562/046
USPC .................................. 600/300–301
See application file for complete search history.

(56) References Cited

U.S. PATENT DOCUMENTS

| | | | | |
|---|---|---|---|---|
| 6,108,685 | A * | 8/2000 | Kutzik et al. | 709/200 |
| 6,280,409 | B1 * | 8/2001 | Stone et al. | 604/67 |
| 6,282,531 | B1 * | 8/2001 | Haughton et al. | 706/50 |
| 6,640,212 | B1 * | 10/2003 | Rosse | 705/7.13 |
| 6,796,799 | B1 * | 9/2004 | Yoshiike et al. | 434/236 |
| 6,821,258 | B2 * | 11/2004 | Reed et al. | 600/595 |
| 6,995,664 | B1 * | 2/2006 | Darling | G08B 19/00 340/10.1 |
| 7,223,234 | B2 * | 5/2007 | Stupp et al. | 600/300 |
| 7,244,231 | B2 * | 7/2007 | Dewing et al. | 600/300 |
| 7,589,637 | B2 * | 9/2009 | Bischoff et al. | 340/573.1 |
| 7,855,650 | B2 * | 12/2010 | Duckert | G08B 21/0423 340/506 |
| 7,937,461 | B2 * | 5/2011 | Kutzik et al. | 709/224 |
| 8,099,427 | B2 * | 1/2012 | Tanigawa | G06Q 10/10 707/769 |
| 8,321,562 | B2 * | 11/2012 | Kutzik et al. | 709/224 |
| 8,589,174 | B2 * | 11/2013 | Nelson et al. | 705/2 |
| 8,608,310 | B2 * | 12/2013 | Otis et al. | 351/159.03 |
| 8,682,952 | B2 * | 3/2014 | Kutzik et al. | 709/200 |
| 8,894,576 | B2 * | 11/2014 | Alwan et al. | 600/301 |
| 9,098,993 | B2 * | 8/2015 | Reed, Jr. | A61B 5/6889 |
| 2003/0179094 | A1 * | 9/2003 | Abreu | 340/573.1 |
| 2005/0131736 | A1 * | 6/2005 | Nelson et al. | 705/2 |
| 2005/0240571 | A1 * | 10/2005 | Haigh | A61B 5/11 |
| 2005/0278409 | A1 * | 12/2005 | Kutzik et al. | 709/200 |
| 2008/0084296 | A1 * | 4/2008 | Kutzik | G06F 19/3418 340/540 |
| 2011/0237905 | A1 * | 9/2011 | Kutzik et al. | 600/300 |
| 2012/0149996 | A1 * | 6/2012 | Stivoric et al. | 600/301 |
| 2012/0245444 | A1 * | 9/2012 | Otis et al. | 600/345 |
| 2014/0074179 | A1 * | 3/2014 | Heldman et al. | 607/45 |
| 2014/0340227 | A1 * | 11/2014 | Reed, Jr. | A61B 5/6889 340/573.1 |

* cited by examiner

SYSTEM AND METHOD FOR THE INFERENCE OF ACTIVITIES OF DAILY LIVING AND INSTRUMENTAL ACTIVITIES OF DAILY LIVING AUTOMATICALLY

CROSS-REFERENCE TO RELATED APPLICATIONS

This application is a continuation of U.S. application Ser. No. 11/076,604, filed Mar. 10, 2005, and titled "System and Method for the Inference of Activities of Daily Living and Instrumental Activities of Daily Living Automatically," which claims the benefit under 35 U.S.C. § 119(e) of U.S. Provisional Application Ser. No. 60/551,894, filed Mar. 10, 2004, the contents of which are hereby incorporated by reference in their entireties.

BACKGROUND OF THE INVENTION

Functional assessment of a person's health status, or recuperation after injury, hospitalization and treatment is of primary concern in medicine. Most branches of Medicine, including geriatrics, rehabilitation and physical therapy, neurology and orthopedics, nursing and elder care research studies currently rely on one of three basic strategies: self-report (either in questionnaires, or structured interviews), observational judgment by professionals or family members (such as the Activities of Daily Living [ADL] scales (Katz 1963), and the Instrumental Activities of Daily Living [IADL] scales (Fillenbaum 1985)), or demonstrated performance of specific skills. Despite being considerably useful, one challenge of these approaches is to relate the findings obtained in the physician's office or research laboratory with the person's function at home (Reuben 1995). An implicit assumption is that an individual's functional ability is independent of the environment. Clinical experience suggests that an individual's functional ability is actually environment-specific, since function increases when subjects are in familiar surroundings due to reduced confusion (Kane 1985). The artificial setting of direct observation in a doctor's office or laboratory setting does not allow the observer to determine the effect of environmental barriers such as unfamiliarity or artificiality on function. Moreover, one-time assessment of function does not allow for assessment of variability of functional performance over the course of a day or several days. Further, one-time measurement of function does not allow for assessment of change, and episodic, rather than continuous measurement of function does not permit determination of the rate of change, a parameter which is vitally important in determining the adequacy of certain clinical services and treatments (such as rehabilitation) following functional loss. The accuracy of a prognosis is improved by measuring the rate of change of a patient's condition.

Since there is little correlation between the presence of a certain disease and its impact on an elder's functional abilities, direct assessment of function is an integral part of geriatric care. For example, an octogenarian with systolic hypertension, congestive heart failure, maturity-onset diabetes mellitus, severe osteoarthritis and a past history of hip fracture might be a vigorous, independent community volunteer, or a frail, highly dependent resident of a nursing home (Fried et al. 1997).

Despite a variety of activities of daily living (ADL) tools developed over the last several decades, a consensus exists with regard to the basic components of such functional assessments. Almost all validated scales include measures of dressing, bathing, toileting, transfer and feeding ability (Fleming et al. 1995). ADL scores indicate the degree to which an individual has independent functioning in each of the self-care areas. However, progress in the assessment of function since the early 1960's has not been well implemented in everyday assessment strategies.

Many devices have been invented to continuously measure the activity levels of patients and to assess their functionality, using piezoelectric sensors and accelerometers (such as that of Dynaport). However, these devices measure activity level and do not really discern, measure or assess the activities of daily living or instrumental activities of daily living (IADL) score comprises six questions that correspond to the individual's ability to bathe, dress, use the toilet, move in out of bed, control their bladder or bowels and feed themselves without help. Similarly, IADL score includes five questions that seek information about the individual's ability to get to places that are outside walking distance, go shopping for groceries, prepare meals, do house work and handle finances without help. None of these devices can automatically infer any the above-mentioned activities specifically.

BRIEF SUMMARY OF INVENTION

The various embodiments of the present invention provide a method and related system that, among other things, automatically infer answers to all of the ADL questions and the first four questions of the IADL in the home. The inference methods detect the relevant activities unobtrusively, continuously, accurately, objectively, quantifiably and without relying on the patient's own memory (which may be fading due to aging or an existing health condition, such as Traumatic Brain Injury (TBI)) or on a caregiver's subjective report. The methods rely on the judicious placement of a number of sensors in the subject's place of residence, including motion detection sensors in every room, the decomposition of each relevant activity into the sub-tasks involved, identification of additional sensors required to detect the relevant sub-tasks and spatial-temporal conditions between the signals of sensors to formulate the rules that will detect the occurrence of the specific activities of interest. The sensory data logged on a computing device (computer, data logger etc.), date and time stamped, is analyzed using specialist data analysis software tools that check for the applicable task/activity detection rules. The methods are particularly useful for the continued in-home assessment of subjects living alone to evaluate their progress in response to medical intervention drug or physical therapy or decline in abilities that may be the indicator of the onset of disease over time. Measuring the frequency of each activity, the time required to accomplish an activity or a subtask and the number of activities/subtasks performed continuously over time can add extremely valuable quantification extensions to the existing ADL and IADL evaluation instruments, as it will not only reveal important information setting up a baseline for activity levels for each activity, but will also easily allow the detection of any drift from these personalized norms.

An aspect of an embodiment of the present invention provides a method to automatically derive answers to the questions of two clinical functional assessment instruments activities of daily living (ADLs), and all but one of the instrumental activities of daily living (IADLs) relying on sensors targeting the side-effects of the activities. This method may comprise: 1) date and time stamping sensor firings; and 2) setting a set of rules method where the spatio-temporal relationships of sensor firings are examined and analyzed to infer the occurrence of activities of interest. Theses rules may include at least one of the following: a rule to automatically bathing/showering; a rule to automatically detect dressing; a rule to automatically detect toileting events; a rule to automatically detect the ability to ambulate (get out of bed/chair); a rule to automatically detect problems in controlling bladder and/or bowels; a rule to automatically detect the ability to feed oneself; a rule to automatically detect the ability to get to places outside of walking distance; a rule to automatically detect the ability to shop for groceries; a rule to automatically detect the ability to prepare meals; and a rule to automatically detect the ability to do house work.

An aspect of an embodiment of the present invention provides a system to automatically derive answers to the questions of two clinical functional assessment instruments activities of daily living (ADLs), and all but one of the instrumental activities of daily living (IADLs). This system may comprise: 1) a sensor module, wherein the sensor module targets the side-effects of the activities; and 2) a processor module, the processor module programmed to a) date and time stamp sensor firings; and b) set a set of rules where the spatio-temporal relationships of sensor firings are examined and analyzed to infer the occurrence of activities of interest. These rules may include at least one of the following: a rule to automatically bathing/showering; a rule to automatically detect dressing; a rule to automatically detect toileting events; a rule to automatically detect the ability to ambulate (get out of bed/chair); a rule to automatically detect problems in controlling bladder and/or bowels; a rule to automatically detect the ability to feed oneself; a rule to automatically detect the ability to get to places outside of walking distance; a rule to automatically detect the ability to shop for groceries; a rule to automatically detect the ability to prepare meals; and a rule to automatically detect the ability to do house work.

An aspect of an embodiment of the present invention provides a computer program product comprising computer useable medium having computer program logic for enabling at least one processor in a computer system to automatically derive answers to the questions of two clinical functional assessment instruments activities of daily living (ADLs), and all but one of the instrumental activities of daily living (IADLs) relying on sensors targeting the side-effects of the activities. This computer logic may comprise: 1) date and time stamping sensor firings; and 2) setting a set of rules method where the spatio-temporal relationships of sensor firings are examined and analyzed to infer the occurrence of activities of interest. These rules may include at least one of the following: a rule to automatically bathing/showering; a rule to automatically detect dressing; a rule to automatically detect toileting events; a rule to automatically detect the ability to ambulate (get out of bed/chair); a rule to automatically detect problems in controlling bladder and/or bowels; a rule to automatically detect the ability to feed oneself; a rule to automatically detect the ability to get to places outside of walking distance; a rule to automatically detect the ability to shop for groceries; a rule to automatically detect the ability to prepare meals; and a rule to automatically detect the ability to do house work.

These and other objects, along with advantages and features of the invention disclosed herein, will be made more apparent from the description, drawings and claims that follow.

BRIEF SUMMARY OF THE DRAWINGS

The accompanying drawings, which are incorporated into and form a part of the instant specification, illustrate several aspects and embodiments of the present invention and, together with the description herein, serve to explain the principles of the invention. The drawings are provided only for the purpose of illustrating select embodiments of the invention and are not to be construed as limiting the invention.

DETAILED DESCRIPTION OF THE INVENTION

The various embodiments of the present invention provide a method and system to, but not limited thereto, automatically infer answers for all of the ADL questions and the first four questions of the IADL in the home. In an embodiment the present invention method automatically infers answers to all ADL question, and thus will be dubbed AADL for Automatic ADL. This method may use a motion detector in each room, humidity sensors, pressure mats, and electronic noses (odor detecting sensors).

Similarly, a second method of the present invention automatically infers answers to four of the IADL question. The fifth question, regarding the individual's ability to handle money and financial transactions without help, could be answered. However, it should be appreciated that it is a sensitive and a confidential matter that may cause problems of guardianship and the like; hence, the answer to this question is best asked directly, rather than inferred automatically, if it is relevant for the purpose of the evaluation. We will dub this method AIADL for Automatic IADL. This method may also use motion detectors in each room, humidity sensors, cabinet door switches, a kitchen food scanner (the subject of a separate disclosure), radio frequency transmitter-receiver, infra red transmitter-receiver, refrigerator door switch, microwave door switch, temperature sensor, humidity sensors and sensors to detect the operation of the washing machine, dishwasher, the vacuum cleaner and the iron. It should be appreciated that additional questions or fewer questions may be implemented as well.

In both methods discussed above, data from the sensors may be logged on a computing device (computer, data logger or a universal data logging and communications module), date and time stamped. The data is analyzed to check the spatial-temporal conditions of sensory data that characterize the relevant subtasks and in turn the activities of interest, using special data analysis software tools. The methods disclosed herein are particularly useful for the continued assessment of subjects living alone in their home to evaluate their progress in response to medical intervention, drug, physical and/or rehabilitation therapy or decline in abilities that may be the indicator of the onset of disease. Nevertheless, the methods apply to situations where more than one person is present in the home, if subjects were identified to the analyzing computer system, such that different activities taking place at the same time could be recognized and linked to a specific user. This can be done via several techniques, including, but not limited to, having the users carry Radio-frequency identification chips (RFID), electronic tags, or electronic communications device (such as Bluetooth devices).

In both methods, the frequency of each activity, the time required accomplishing an activity or a subtask and the number of activities/subtasks performed will be continuously recorded over time. The measurement information will form a norm of personalized activity level, against which the most current activity levels can be compared to detect any drift from this norm.

Figure 1:
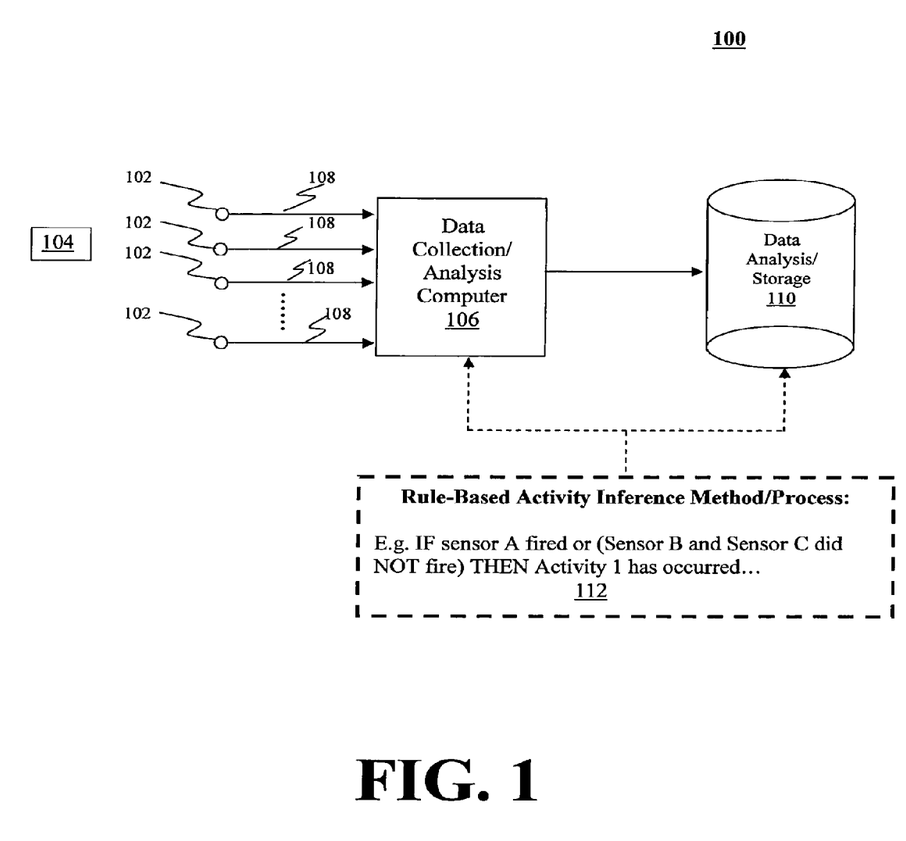
FIG. 1 provides a schematic block diagram of an embodiment of the subject ADL system.

Referring to FIG. 1, FIG. 1 is a schematic block diagram of an embodiment of the subject ADL system 100. Sensors 102 targeting the incidental effects of the activities of interest are embedded/distributed in the living space or area (not shown) of the patient 104. The sensors 102 communicate with a data/collection analysis computer/processor 106 via hard wire or wireless connection 108. The collected/analyzed data may be stored in storage/archive 110. The rule based algorithms and methods 112 may be applied to and implemented with the computer/processor 106 and storage/archive 110.

1—Method for the Inference of Automatic Activities of Daily Living (AADL):

Before describing an embodiment of the present invention method in detail, we will list the ADL questions that are conventionally asked in interviews with patients during their visits to the physician. We will later take each of these questions, decompose its main activity into subtasks, identify the sensors needed to detect the subtasks/activity, determine the necessary and sufficient logical conditions governing the spatial-temporal relationship between sensors' signals that allow it to infer the answer, and will finally describe how the answer can be inferred automatically.

Questions for evaluating the Activities of Daily Living are:

1. Do you bathe yourself without help?
2. Do you dress yourself without help?
3. Do you use the toilet without help?
4. Do you move in and out of bed without help?
5. Do you have any trouble controlling your bladder or your bowels?
6. Do you feed yourself without help?

(Adapted from: Katz S, Ford A B, Moskowitz R W, Jackson B A, Jaffe M W, Cleveland M A. The index of ADL: A standardized measure of biological and psychosocial function. *JAMA*. 1963; 185:914-919.)

The automatic inference of answers to these questions relies on a required set of sensors relevant to the activity and all its related subtasks, a data logging system and a computer running a software program that implements the check on the conditions characterizing the activity. In what follows we will outline an embodiment of the sensors required for question/activity and sufficient conditions.

Do You Bathe Yourself without Help?

To automatically infer the answer to this question, we need to establish that the subject is either alone at home, or that he/she carried out the bathing activity alone and without help from others. The person can be confirmed alone if the array of motion sensors (one in each room) fire only in one room at a time with a clear spatial-temporal relation between sensor firings that is sensible with respect to the floor plan. However, motion detected only in one room, the bedroom for instance, followed by motion detected in the bathroom, without any motion detected in the hallway connecting between the two rooms in the period between the two sensors' firings is an indicator of more than one person in the home. Similarly, simultaneous motion sensor firings in different rooms are also indicative of the presence of others in the home.

Unfortunately, low-cost motion detecting sensors will not be able to differentiate the motion of one person from that of two persons moving together. Hence, it is necessary to establish, with a high degree of likelihood, that the subject is alone when they have bathed, through confirmation that the front door motion sensor, and the geographically subsequent sensors, did not fire prior the bathing action. Thus we can establish that no one came into the home to accompany the subject into the bathroom to help him or her bathe.

Additionally, if other motion sensors' information indicates the presence of another person in the home, in addition to the monitored subject, before bathing took place, then we must establish that the subject bathed on their own. This can be established by continued sensor activity outside the bathroom while the subject is bathing/showering.

Bathing activity can be established if the bathroom motion sensor fired and the output signal of a humidity sensor placed in the bathroom extremely increased, and the subject remained in the bathroom for a period of time indicative of a bath or a shower (normally 8 minutes or more). To differentiate between bathing and acts associated with increased humidity in the bathroom, like washing the hands and the face with hot water or shaving, a presence sensor (pressure mat or infra red beam break for example) must be placed in front of the sink; when a person stands on the mat it will generate a binary one signal, however, when the subject is in the bathtub or the shower, the output of the pressure mat is zero.

Consequently, the detection of the activity of bathing requires, in addition the motion detection in every room, a pressure mat in front of the bathroom sink and a humidity sensor in the bathroom.

The inference rule will be:

If {(Subject went into the bathroom) AND (Subject remained in the bathroom for 8 minutes or more) AND (Humidity excessively increased during the activity period) AND (Subject was NOT standing on the pressure mat placed in front of the bathroom sink during the activity period)} AND {[(Subject is alone at home) AND (There is NOT any indication from the motion sensors of any visitors coming into the residence through outdoor(s) prior to the activity)] OR [(Subject has company) AND (Motion Sensors show continued activity during the activity period outside the bathroom)]}, Then Subject has bathed without help.

The logical spatial temporal conditions embraced by the first set of brackets, characterize the concerned activity, bathing for this particular question, where as the set of conditions embraced by the second set of brackets establish that the subject is either alone or did not receive help of another person during the activity. If the activity conditions were True, i.e. the activity has taken place, but the second set of condition could not be confirmed, the inference system can report bathing probably with the help of others. The percentage of help with the activity can be estimated from the ratio between the periods of time when no motion detected outside the bathroom (or the room where the activity takes place in general), to the time taken to perform the activity. The estimated percentage of help, together with the frequency of the activity, and the time required to carry-out the activity will allow attaching a value that quantifies the response, rather than having a yes or no answer to the questions. The help estimate, the frequency and time required to do accomplish the activity are generic and can be applied to quantify the answer for all of the traditional ADL/IADL questions.

Do You Dress Yourself without Help?

The answer to this question can be formulated in the following rule:

If {(Subject went out of their residence)} AND {[(Subject is alone at home) AND (There is NOT any indication from the motion sensors of any visitors coming into the residence through outdoor(s) prior to the activity)] OR [(Subject has company) AND (Motion Sensors show continued activity during the activity period outside the bedroom)]}, Then Subject has been able to dress without help.

This is true, because normally people get dressed before leaving their homes, and they usually get dressed in the bedroom. We can establish that the subject went out of their residence through tracking the subject's movement, from the signal of the motion detectors, towards the exit door and then disappearing form the sensors for some time.

Do You Use the Toilet without Help?

This question can be answered using the following rule:

If {(Subject went into the bathroom) AND (Subject remained in the bathroom for some time) AND (Subject was NOT standing on the pressure mat placed in front of the bathroom sink during the activity period) AND (Humidity did NOT excessively increased during the activity period) AND (an electronic nose detected characteristic odors) AND (Toilet was flushed)} AND {[(Subject is alone at home) AND (There is NOT any indication from the motion sensors of any visitors coming into the residence through outdoor(s) prior to the activity)] OR [(Subject has company) AND (Motion Sensors show continued activity during the activity period outside the bathroom)]}, Then Subject has used the toilet without help.

The use of an electronic nose to detect odors characteristic of using the bathroom is not absolutely necessary, however it provides confirmation. Hence, it is best to install an electronic nose in the bathroom tuned to detect such odors. Toilet flushing can be detected via a tilt switch attached to the float in the tank or to the flushing handle.

Do You Move in and Out of Bed or Chair without Help?

The answer to this question can be automatically inferred by the two following rules:

If {(Subject is lying in bed) AND (Subject Stood up)} AND {[(Subject is alone at home) AND (There is NOT any indication from the motion sensors of any visitors coming into the residence through outdoor(s) prior to the activity)] OR [(Subject has company) AND (Motion Sensors show continued activity during the activity period outside the bedroom)]}, Then Subject has moved out of bed without help.

A sensor (pressure mat, load cell, pressure bladder or similar) placed under the bed's mattress to detect lying in bed, and another sensor on the floor at the exit point of the bed to detect standing up are required. Similarly, the activity of moving in and out of a chair can be detected by using the same rule and placing sensors under chair cushions and in front of commonly used chairs.

If {(Subject is sitting in chair) AND (Subject Stood up)} AND {[(Subject is alone at home) AND (There is NOT any indication from the motion sensors of any visitors coming into the residence through outdoor(s) prior to the activity)] OR [(Subject has company) AND (Motion Sensors show continued activity during the activity period outside the room)]}, Then Subject has moved out of the chair without help.

Do You have any Trouble Controlling Your Bladder or Bowels?

The answer to this question can be automatically inferred by installing an electronic nose that can detect characteristic odors in the following places: the bedroom, the laundry room and/or near the usual place where the subject keeps dirty laundry before it is washed (e.g. laundry basket).

Do You Feed Yourself without Help?

Usually, feeding involves preparing a meal before eating, and cleaning up after. Hence; one way to answer this question unobtrusively is the following rule:

If {(Subject is in the kitchen) AND (There are activities in the kitchen) AND [(There is an increase in the temperature over the stove, range, or oven) OR (Use of microwave oven)] AND [(Dishwasher door open) OR (Increase of humidity over the kitchen sink)]} AND {[(Subject is alone at home) AND (There is NOT any indication from the motion sensors of any visitors coming into the residence through outdoor(s) prior to the activity)] OR [(Subject has company) AND (Motion Sensors show continued activity during the activity period outside the kitchen)]}, Then Subject has prepared a meal, cleaned up and fed themselves without help.

Activities that are indicative of preparing a meal in the kitchen include any change of status detected from the kitchen cabinets and drawers' switches, refrigerator door switch, microwave door switch and the like.

An electronic nose, tuned to detect cooking odors, can placed in the kitchen to give added confirmation of the activity of cooking, but is not absolutely necessary. The humidity sensor, positioned over the kitchen sink will detect washing up the dishes after the meal.

However, a person may prepare the meal, eat and postpone the cleaning till later. In this case, the following rule may be sufficient:

If {(Subject is in the kitchen) AND (There are activities in the kitchen) AND [(There is an increase in the temperature over the stove, range, or oven) OR (Use of microwave oven)]} AND {[(Subject is alone at home) AND (There is NOT any indication from the motion sensors of any visitors coming into the residence through outdoor(s) prior to the activity)] OR [(Subject has company) AND (Motion Sensors show continued activity during the activity period outside the kitchen)]}, Then Subject has prepared a meal and fed themselves without help.

The first rule is indicative more of completing all the subtasks involved in the direct feeding process and hence would score more points; this also reflects getting a higher score for being more active by doing an additional task, in this case washing dishes after the meal.

2—Method for the Inference of Automatic Instrumental Activities of Daily Living (AIADL):

The questions that are asked of patients to infer Instrumental Activities of Daily Living are:
1—Can you get to places outside of walking distance without help (for example travel alone on buses, taxis, or drive a car)?
2—Can you go shopping for groceries without help? (Assumes the patient has transportation).
3—Can you prepare your own meals without help?
4—Can you do your housework without help?
5—Can you handle your own money without help (for example, write checks, pay bills)?

(Adapted from Fillenbaum G G. Screening the elderly: A brief instrumental activities of daily living measure. *J Am Geriatr Soc.* 1985; 33:698-706.)

In the following section we will discuss each of these questions and provide rules for the automatic inference of its answer:

Can You Get to Places Outside of Walking Distance without Help?

To infer the answer to this question automatically we can partially rely on the rule used in the inference of the answer to the second ADL question, regarding the subject's ability to get dressed without help, and add another condition on the distance. Hence the rule would be:

If {(Subject went out of their residence) AND (The trip made is longer than a preset distance)} AND {[(Subject is alone at home) AND (There is NOT any indication from the motion sensors of any visitors coming into the residence through outdoor(s) prior to the activity)] OR [(Subject has company) AND (Motion Sensors show continued activity in the residence after the subject has left)]}, Then Subject has gone places outside of walking distance without help.

We can establish that the subject went to a place outside of walking distance if the subject is carries a radio frequency transmitter with a pre-set range, with the receiver fixed in the subject's residence. A wireless communications device operating in extended Bluetooth mode may be sufficient for this purpose.

Can You go Shopping for Groceries without Help?

The inference of an answer to this question is twofold; the first involves going out with out help, and while the second coming back alone with groceries. Hence the inference rule can be formulated as follows:

If {(Subject went out of their residence) AND (Sensors' signals are indicative of putting groceries away, after their return)} AND {[(Subject is alone at home) AND (There is NOT any indication from the motion sensors of any visitors coming into the residence through entry door(s) prior to the activity)] OR [(Subject has company) AND (Motion Sensors show continued activity in the residence after the subject has left)] AND (Subject returned home alone)}, Then Subject has gone shopping for groceries without help.

The sensors' signals indicative of putting groceries away after return include setting off kitchen cabinets, drawers and refrigerator door switches. Moreover, we can establish if the subject returned to the residence alone from comparing motion sensor activities before and after the arrival of the subject to determine if more than one person are in the home, after the shopping trip if the subject was alone before the shopping trip and if there is indication of additional people in the home after the shopping trip, if the subject had company before the shopping trip.

A better confirmation of shopping for groceries will be provided if the home was equipped with a food scanner and the subject scanned groceries before storing them away; the kitchen scanner is the subject of a separate disclosure.

Can You Prepare Your Own Meals without Help?

The rule to infer the answer to this question is already included in the question related to the subject's ability to feed himself/herself form the ADL instrument. The extracted rule is as follows:

If {(Subject is in the kitchen) AND (There are activities in the kitchen) AND [(There is an increase in the temperature over the stove, range, or oven) OR (Use of microwave oven)]} AND {[(Subject is alone at home) AND (There is NOT any indication from the motion sensors of any visitors coming into the residence through outdoor(s) prior to the activity)] OR [(Subject has company) AND (Motion Sensors show continued activity during the activity period outside the kitchen)]}, Then Subject has prepared a meal and fed themselves without help.

Can You do Your Housework without Help?

Cleaning and housework are varied; they primarily include, among other things, washing clothes and drying them, washing dishes, ironing and vacuuming. Thus the rule to infer the answer to this question automatically can be formulated as follows:

If {(The cabinet(s) containing the cleaning materials is opened) OR (There is an increase of humidity over the kitchen sink) OR (Dishwasher turned on) OR (Vacuum cleaner is turned on) OR (Washing machine is turned on) OR (Tumble dryer is turned on) OR (Iron turned on)} AND {[(Subject is alone at home) AND (There is NOT any indication from the motion sensors of any visitors coming into the residence through outdoor(s) prior to the activity)] OR [(Subject has company) AND (Motion Sensors show continued activity during the activity period outside the room where the activity is taking place)]}, Then Subject has done housework without help.

The scoring of this particular rule can be made proportional to the number of activities performed consecutively, indicating a session of housework. The detection of these activities requires determining cabinet(s) where cleaning materials are kept (such as under kitchen and bathroom sinks), and adding switches to detect activities involving these cabinets. Moreover, the operation of the electric appliances used in the bulk of housework, can be achieved using wireless on/off sensors for portable appliances, such as the vacuum cleaner and iron, and magnetic reed switches to detect the status of the fixed appliances (such as a washing machine or a dryer). The humidity sensor placed over the kitchen sink would detect activity involving the use of water, such as dishwashing.

Can You Handle Your Own Money without Help?

We can unobtrusively establish if the subject can handle their own money, indirectly from the continuation of services, such as electricity supply, phone since this indicates payment of bills. However, it is more difficult to confirm whether the subject is handling their finances on their own unobtrusively. Moreover, the question is sensitive, particularly to the elders as it may open doors for guardianship issues. Thus, we feel that it would be best to get this confirmation from the subject by directly asking this question during the visit to the family physician.

Figure 2:
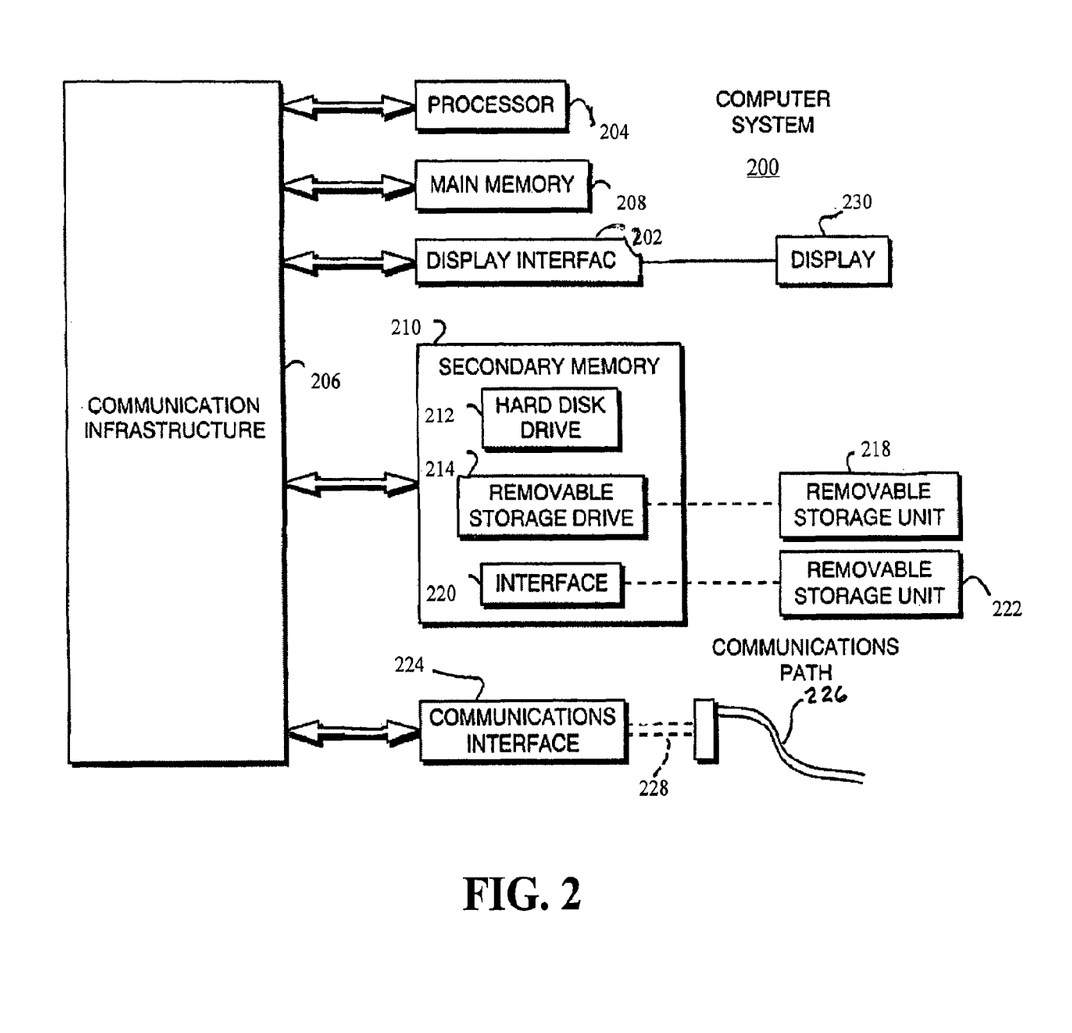
FIG. 2 provides a functional block diagram for an illustrative computer system for implementation of an embodiment of the present invention.

Next, as best shown in FIG. 2, an embodiment of the present invention method may be implemented using hardware, software or a combination thereof and may be implemented in one or more computer systems or other processing systems, such as personal digit assistants (PDAs). In an example embodiment, the invention was implemented in software running on a general purpose computer 200 as illustrated in FIG. 2. Computer system 200 includes one or more processors, such as processor 204. Processor 204 is connected to a communication infrastructure 206 (e.g., a communications bus, cross-over bar, or network). Computer system 200 may include a display interface 202 that forwards graphics, text, and other data from the communication infrastructure 206 (or from a frame buffer not shown) for display on the display unit 230.

Computer system 200 also includes a main memory 208, preferably random access memory (RAM), and may also include a secondary memory 210. The secondary memory 220 may include, for example, a hard disk drive 212 and/or a removable storage drive 214, representing a floppy disk drive, a magnetic tape drive, an optical disk drive, a flash memory etc. The removable storage drive 214 reads from and/or writes to a removable storage unit 218 in a well known manner. Removable storage unit 218, represents a floppy disk, magnetic tape, optical disk, etc. which is read by and written to by removable storage drive 214. As will be appreciated, the removable storage unit 218 includes a computer usable storage medium having stored therein computer software and/or data.

In alternative embodiments, secondary memory 210 may include other means for allowing computer programs or other instructions to be loaded into computer system 200.

Such means may include, for example, a removable storage unit 222 and an interface 220. Examples of such removable storage units/interfaces include a program cartridge and cartridge interface (such as that found in video game devices), a removable memory chip (such as a ROM, PROM, EPROM or EEPROM) and associated socket, and other removable storage units 222 and interfaces 220 which allow software and data to be transferred from the removable storage unit 222 to computer system 200.

Computer system 200 may also include a communications interface 224. Communications interface 224 allows software and data to be transferred between computer system 200 and external devices. Examples of communications interface 224 may include a modem, a network interface (such as an Ethernet card), a serial or parallel communications port, a PCMCIA slot and card, a modem etc. Software and data transferred via communications interface 224 are in the form of signals 228, which may be electronic, electromagnetic, optical or other signals capable of being received by communications interface 224. Signals 228 are provided to communications interface 224 via a communications path (i.e., channel) 226. A channel 226 (or any other communication means or channel disclosed herein) carries signals 228 and may be implemented using wire or cable, fiber optics, a phone line, a cellular phone link, an RF link, an infrared link and other communications channels.

In this document, the terms "computer program medium" and "computer usable medium" are used to generally refer to media such as removable storage drive 214, a hard disk installed in hard disk drive 212, and signals 228. These computer program products are means for providing software to computer system 200. The invention includes such computer program products.

Computer programs (also called computer control logic) are stored in main memory 208 and/or secondary memory 210. Computer programs may also be received via communications interface 224. Such computer programs, when executed, enable computer system 200 to perform the features of the present invention as discussed herein. In particular, the computer programs, when executed, enable processor 204 to perform the functions of the present invention. Accordingly, such computer programs represent controllers of computer system 200.

In an embodiment where the invention is implemented using software, the software may be stored in a computer program product and loaded into computer system 200 using removable storage drive 214, hard drive 212 or communications interface 224. The control logic (software), when executed by the processor 204, causes the processor 204 to perform the functions of the invention as described herein.

In another embodiment, the invention is implemented primarily in hardware using, for example, hardware components such as application specific integrated circuits (ASICs). Implementation of the hardware state machine to perform the functions described herein will be apparent to persons skilled in the relevant art(s).

In yet another embodiment, the invention is implemented using a combination of both hardware and software.

In an example software embodiment of the invention, the methods described above may be implemented in various programs and programming language known to those skilled in the art.

The various embodiments of the present invention may be implemented with the systems and methods disclosed in the following U.S. patents of Table 1, and of which are hereby incorporated by reference herein in their entirety:

TABLE 1

| U.S. Pat. No. | Issue Date | Title |
|---|---|---|
| 6,524,239 | Feb. 25, 2003 | Apparatus for non-intrusively measuring health parameters of a subject and method of use thereof |
| 6,108,685 | Aug. 22, 2000 | System for Generating Periodic Reports Generating Trend Analysis and Intervention for Monitoring Daily Living Activity; |
| 5,692,215 | Nov. 25, 1997 | System for Generating Periodic Reports, Generating Trend Analysis, and Intervention in Accordance with Trend Analysis From a Detection Subsystem for Monitoring Daily Living Activity |
| 6,282,531 | Aug. 28, 2001 | System for managing applied knowledge and workflow in multiple dimensions and contexts |
| 6,165,143 | Dec. 26, 2000 | Method for measuring and indicating the extent to which an individual is limited in daily life activities |
| 6,280,409 | Aug. 28, 2001 | Medical for tracking patient functional status |
| 4,747,120 | May 24, 1988 | Automatic personnel monitoring system |
| 4,952,928 | Aug. 28, 1990 | Adaptable electronic monitoring and identification system |
| 5,032,823 | Jul. 16, 1991 | Secure personnel monitoring system |
| 5,673,692 | Oct. 7, 1997 | Single site, multi-variable patient monitor |
| 4,353,375 | Oct. 12, 1982 | Activity monitor for ambulatory subjects |
| 5,682,882 | Nov. 4, 1997 | Vigilance monitor system |
| 4,286,331 | Aug. 25, 1981 | Monitoring and signaling system including apparatus for processing and analyzing signals produced by activity monitoring sensors |
| 3,803,579 | Apr. 9, 1974 | Automatic Alarm System For Bathroom |
| 3,885,235 | May 20, 1975 | Resettable timer-alarm device used in monitoring geriatric patients |
| 5,967,975 | Oct. 19, 1999 | Home health parameter monitoring system |
| 5,339,821 | Aug. 23, 1994 | Home medical system and medical apparatus for use therewith |
| 5,576,952 | Nov. 19, 1996 | Medical alert distribution system with selective filtering of medical information |
| 5,785,650 | Jul. 28, 1998 | Medical system for at-home patients |
| 4,454,502 | Jun. 12, 1984 | Apparatus for monitoring and signaling system |
| 4,303,801 | Dec. 1, 1981 | Apparatus for monitoring and signaling system |
| 4,281,394 | Jul. 28, 1981 | Monitoring and signaling system including apparatus for processing binary signals having multiple messages |
| 6,290,646 | Sep. 18, 2001 | Apparatus and method for monitoring and communicating wellness parameters of ambulatory patients |
| 5,767,791 | Jun. 16, 1998 | Low-Power circuit and method for providing rapid frequency lock in a wireless communications device |
| 5,410,471 | Apr. 25, 1995 | Networked health care and monitoring system |
| 6,050,940 | Apr. 18, 2000 | General-purpose medical instrumentation |
| 6,080,106 | Jun. 27, 2000 | Patient interface system with a scale |
| 6,206,829 | Mar. 27, 2001 | Computerized medical diagnostic and treatment advice system including network access |
| 6,402,691 | Jun. 11, 2002 | In-home patent monitoring system |
| 3,572,316 | Mar. 23, 1971 | Physiological signal monitoring system |
| 4,838,275 | Jun. 13, 1989 | Home medical surveillance system |
| 5,462,051 | Oct. 31, 1995 | Medical communication system |
| 5,905,436 | May 18, 1999 | Situation Based Monitoring System |
| 6,171,237 | Jan. 9, 2001 | Remote health monitoring system |
| 6,220,101 | Apr. 24, 2001 | Apparatus for Measuring Multiple Pressures |
| 6,348,867 | Feb. 19, 2002 | Control System for building automation control by human physiological signals |
| 6,433,690 | Aug. 13, 2002 | Elderly Fall Monitoring Method and Device |
| 6,445,298 | Sep. 3, 2002 | System and Method for remotely monitoring movement of individuals |
| 4,259,548 | Mar. 31, 1981 | Apparatus for monitoring and signaling system |

The various embodiments of the present invention may be implemented with the systems and methods disclosed in the following PCT International Applications, and of which are commonly owned by the present assignee and are hereby incorporated by reference herein in their entirety: International Patent Application No. PCT/US04/09098, entitled "Method and System for the Derivation of Human Gait Characteristics and Detecting Fall Passively from Floor Vibrations," filed Mar. 26, 2004 and International Patent Application No. PCT/US04/09099, entitled "System and Method for Passive Monitoring of Blood Pressure and Pulse Rate," filed Mar. 26, 2004.

PUBLICATIONS

The following references are hereby incorporated by reference herein in their entirety:
1—Fillenbaum G G. Screening the elderly: A brief instrumental activities of daily living measure. *J Am Geriatr Soc.* 33:698-706 (1985).
2—Fleming K C, Evans J M, Weber D C, Chutka D S. Practical Functional Assessment of Elderly Persons: A Primary-Care Approach. Mayo Clin Proc. 70:890-910 (1995).
3—Fried L P, Guralnik J M. Disability in Older Adults: Evidence regarding significance, etiology, and risk. J Amer Geriatr Soc. 45:92-100 (1997).
4—Kane R, Assessing the Elderly in A. Monk (Ed.), Handbook of Gerontological Services. New York, Van Nostrand Reinold Company, (1985).
5—Katz S, Ford A B, Moskowitz R W, Jackson B A, Jaffe M W, Cleveland M A. The index of ADL: A standardized measure of biological and psychosocial function. *JAMA.* 185:914-919 (1963).
6—Reuben D B. What's wrong with ADLs? J Am Geriatr Soc. 43:936-7 (1995).

It should be understood that while the method described was presented with a certain ordering of the steps, it is not our intent to in any way limit the present invention to a specific step order. It should be appreciated that the various steps can be performed in different orders, for example, the type and number of survey questions may altered. Further, we have described herein the novel features of the present invention, and it should be understood that we have not included details well known by those of skill in the art, such as the design of various types of sensor devices.

Still other embodiments will become readily apparent to those skilled in this art from reading the above-recited detailed description and drawings of certain exemplary embodiments. It should be understood that numerous variations, modifications, and additional embodiments are possible, and accordingly, all such variations, modifications, and embodiments are to be regarded as being within the spirit and scope of the appended claims. For example, regardless of the content of any portion (e.g., title, section, abstract, drawing figure, etc.) of this application, unless clearly specified to the contrary, there is no requirement for any particular described or illustrated activity or element, any particular sequence of such activities, any particular size, speed, dimension or frequency, or any particular interrelationship of such elements. Moreover, any activity can be repeated, any activity can be performed by multiple entities, and/or any element can be duplicated. Further, any activity or element can be excluded, the sequence of activities can vary, and/or the interrelationship of elements can vary. Accordingly, the descriptions and drawings are to be regarded as illustrative in nature, and not as restrictive.

We claim:

1. An automated method of inferring an activity of daily living of a human subject, the method comprising:
    date and time stamping sensor readings from a plurality of sensors;
    storing a computer-readable log of the date and time stamped sensor readings; and
    a computer processor obtaining the stored date and time stamped sensor readings and applying a set of rules that analyze spatial-temporal relationships of multiple sensors' readings to automatically infer that the human subject has engaged in a predetermined activity of interest,
    wherein said spatial-temporal relationships are defined as sequences of said multiple sensors' readings and locations of said plurality of sensors, and
    wherein the computer processor inferring that the subject has engaged in the activity of interest includes the computer processor making an inference as to whether the subject has engaged in the activity of interest without assistance from another person.

2. The method of claim 1, wherein the plurality of sensors are disposed in different rooms of a living area, and the inference that the subject has engaged in the activity of interest without assistance from another person includes application of a rule that (a) recognizes that the activity of interest is taking place in a first room of the living area, (b) infers that another person is present in the living area, and (c) infers that the subject has engaged in the activity of interest without assistance from the other person based on continued sensor activity outside the first room while the subject is engaging in the activity of interest.

3. The method of claim 1, wherein said rules include a rule that infers bathing/showering of the subject based on time and readings from at least a humidity sensor and a presence sensor.

4. The method of claim 3, wherein the rule that infers the bathing/showering of the subject discriminates between other events that would raise humidity in a room where the activity of interest is detected.

5. The method of claim 1, wherein said rules include a rule that infers the ability of the subject to prepare cooked meals based on time and readings from at least a temperature sensor and a presence sensor.

6. The method of claim 1, wherein said rules include a rule that infers the ability of the subject to use the toilet.

7. The method of claim 6, wherein the rule that infers the ability of the subject to use the toilet discriminates between toileting and other predetermined events that would take place in a room where the activity of interest is detected.

8. The method of claim 1, wherein said rules include a rule that infers the ability of the subject to perform a predetermined ambulatory activity without assistance.

9. The method of claim 8, wherein the rule that infers the ability of the subject to perform the predetermined ambulatory activity includes consideration of motion sensor readings showing continued activity during the activity period outside of a room where the activity of interest is detected.

10. The method of claim 1, wherein the inference as to whether the subject has engaged in the activity of interest without assistance from another person is based on a historical analysis of motion detected prior to the activity of interest in a plurality of locations.

11. A system for inferring an activity of daily living of a human subject, the system comprising:
    a plurality of sensors disposed in different rooms of a living area; and
    a microprocessor configured to:
        receive multiple sensor readings from the plurality of sensors;
        store a time stamped log of the sensor readings; and
        apply a set of rules that analyze spatial-temporal relationships of multiple sensor readings to automatically infer that the human subject has engaged in a predetermined activity of interest, wherein said spatial-temporal relationships are defined as sequences of said multiple sensor readings and locations of said plurality of sensors, and wherein the microprocessor is further configured to infer whether the subject has engaged in the activity of interest without assistance from another person based on a historical analysis of motion detected prior to the activity of interest in a plurality of locations.

12. The system of claim 11, wherein the inference that the subject has engaged in the activity of interest without assistance from another person includes application of a rule that (a) recognizes that the activity of interest is taking place in a first room of the living area, (b) infers that another person is present in the living area, and (c) infers that the subject has engaged in the activity of interest without assistance from the other person based on continued sensor activity outside the first room while the subject is engaging in the activity of interest.

13. The system of claim 11, wherein said rules include a rule that infers bathing/showering of the subject based on time and readings from at least a humidity sensor and a presence sensor.

14. The system of claim 13, wherein the rule that infers the bathing/showering of the subject discriminates between other events that would raise humidity in a room where the activity of interest is detected.

15. The system of claim 11, wherein said rules include a rule that infers the ability of the subject to prepare cooked meals based on time and readings from at least a temperature sensor and a presence sensor.

16. The system of claim 11, wherein said rules include a rule that infers the ability of the subject to use the toilet and that discriminates between toileting and other predetermined events that would take place in a room where the activity of interest is detected.

17. The system of claim 11, wherein said rules include a rule that infers the ability of the subject to perform a predetermined ambulatory activity without assistance.

18. The system of claim 17, wherein the rule that infers the ability of the subject to perform the predetermined ambulatory activity includes consideration of motion sensor readings showing continued activity during the activity period outside of a room where the activity of interest is detected.

19. A computer program product comprising non-transitory computer readable storage medium having computer program logic that causes at least one processor in a computer system to perform operations including:

date and time stamping sensor readings from a plurality of sensors;

storing a log of the date and time stamped sensor readings; and applying a set of rules by a computer processor that analyze spatial-temporal relationships of multiple sensors' readings to automatically infer that the human subject has engaged in a predetermined activity of interest, wherein said spatial-temporal relationships are defined as sequences of said multiple sensors' readings and locations of said multiple sensors, and wherein the inference by the computer processor that the subject has engaged in the activity of interest includes an inference by the computer processor as to whether the subject has engaged in the activity of interest without assistance from another person based on a historical analysis of motion detected prior to the activity of interest in a plurality of locations.

20. The computer program product of claim 19, wherein said rules include rules that infer at least three of:

bathing/showering of the subject based on time and readings from at least a humidity sensor and a presence sensor;

the ability of the subject to prepare cooked meals based on time and readings from at least a temperature sensor and a presence sensor;

the ability of the subject to use the toilet; and/or the ability of the subject to perform a predetermined ambulatory activity without assistance.

* * * * *